United States Patent

Müller

[11] 3,986,934
[45] Oct. 19, 1976

[54] APPARATUS FOR AEROBIC CULTIVATION OF MICRO-ORGANISMS

[76] Inventor: Hans Müller, Im Almendli, Erlembach,, Switzerland

[22] Filed: Aug. 22, 1974

[21] Appl. No.: 499,585

[30] Foreign Application Priority Data
Aug. 30, 1973 Switzerland.................. 12491/73

[52] U.S. Cl................................ 195/142; 195/143; 261/87
[51] Int. Cl.²........................................... C12B 1/16
[58] Field of Search ............... 195/142, 143; 261/87

[56] References Cited
UNITED STATES PATENTS

| | | |
|---|---|---|
| 2,522,947 | 9/1950 | Hatch et al. ........................ 195/143 |
| 2,966,345 | 12/1960 | Burgoon et al. ...................... 261/87 |
| 2,997,424 | 8/1961 | Mayer .................................. 261/87 |
| 3,650,513 | 3/1972 | Werner ................................ 261/87 |
| 3,681,200 | 8/1972 | Ridgway, Jr. ...................... 195/142 |
| 3,722,679 | 3/1973 | Logue .................................. 261/87 |
| 3,847,750 | 11/1974 | Ridgway, Jr. ...................... 195/142 |

Primary Examiner—Alvin E. Tanenholtz
Attorney, Agent, or Firm—Michael J. Striker

[57] ABSTRACT

A fermentation vessel has a tubular guide baffle, including a tubular member extending through it. A bundle of heat-exchange tubes extends through the tubular member. An impeller is located at one end of the baffle and circulates a mixture of a gaseous and a liquid phase through the same. Heat-exchange fluid is also circulated through the baffle.

12 Claims, 7 Drawing Figures

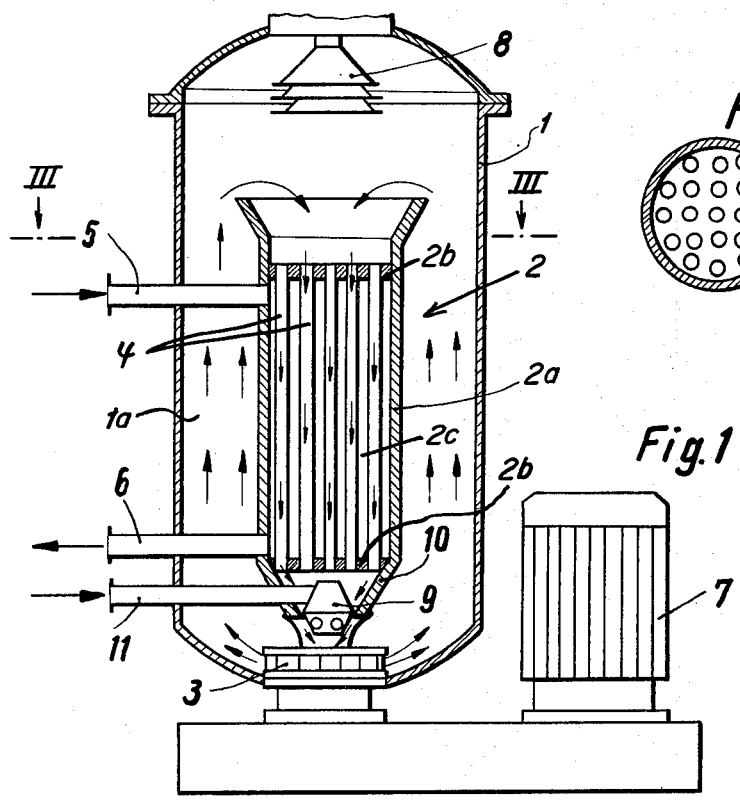
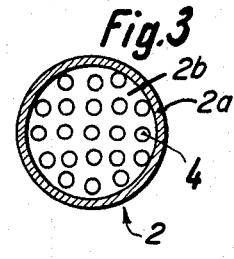
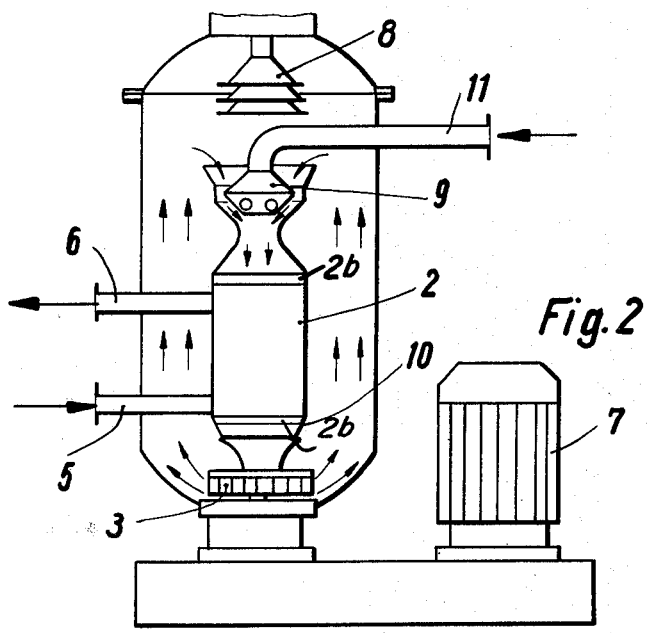
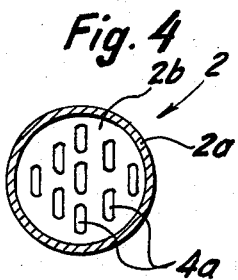

APPARATUS FOR AEROBIC CULTIVATION OF MICRO-ORGANISMS

BACKGROUND OF THE INVENTION

This invention relates to apparatus for the aerobic cultivation of micro-organisms, such as bacteria, yeasts, algae, fungi, etc.

The aerobic cultivation of such micro-organisms is becoming of increasingly greater importance, and is being carried out on an ever larger scale. In many instances of such cultivation, the metabolic and growth processes which take place during the cultivation are strongly exothermic, i.e. they take place under liberation of substantial amounts of heat. This heat must be removed, because otherwise the temperature prevailing in the equipment which is used to carry out the cultivation, would rise to a level at which it could inhibit the growth of the micro-organisms or at which it might even destroy the latter.

For example, depending upon whether the fermentation medium used for the growth of yeasts is a carbohydrate, an alcohol, an acid or a hydrocarbon, the heat liberated per kilogram of yeast produced by cultivation amounts to between 3–9000 kcal.

The removal of this liberated heat presents a problem, especially when very rapid fermentation at high production rates is desired, as in the cultivation of single cell proteins (S.C.P.) The amount of heat generated under these circumstances can be so high as to require very highly efficient cooling of the cultivating medium. Thus, in the cultivation of nutrient yeasts, which at the present state of the art can be carried out at generating times of 1.5 to 2.5 hours, several million kcal. of heat must be removed each hour from a fermentation vessel having a capacity of 200–300 cubic meters of fermentation medium.

The fermentation temperature, at which the micro-organisms will properly grow under optimum conditions, is relatively low, being on the order of 30°–40° C. Since the amount of cooling medium (usually water) that is available is frequently restricted, and since the available water is frequently not very cold, it is necessary to incorporate very efficient heat-exchange arrangements in the cultivating equipment, in order to be able to remove the large amounts of undesired heat despite the aforementioned difficulties.

The prior art contains various proposals for dealing with this problem; however, experience has shown that none of these are as effective as is desired.

SUMMARY OF THE INVENTION

Accordingly, it is an object of the invention to provide an improved apparatus for the aerobic cultivation of micro-organisms.

More particularly, it is an object of the invention to provide such an apparatus which makes it possible to reliably maintain the temperature of the fermentation medium at a selected level, for example at a level between 30° and 40° C.

Another object of the invention is to provide such an apparatus which includes an advantageous arrangement for introducing a gaseous phase into the fermentation medium, for aeration of the same.

In keeping with these objects, and with others which will become apparent hereafter, one feature of the invention resides in an apparatus of the type under discussion which, briefly stated, comprises a fermentation vessel having an interior chamber for the fermentation-supporting liquid phase and a gaseous phase. A tubular guide baffle is mounted in this chamber and has spaced open end portions; it includes a tubular element and a bundle of substantially parallel heat-exchange tubes mounted in this element. Inlet and outlet means communicate with this baffle for circulating a heat-exchange medium through the same.

Impeller means is mounted at one of the open end portions of the guide baffle for creating a flow of the phases through the interior chamber and through the guide baffle axially of the latter. In this manner, aeration of the liquid phase with the gaseous phase is obtained at the same time as the phases exchange heat with the heat-exchange medium flowing through the guide baffle, so that the phases can be reliably maintained at a constant uniform temperature which is required for optimum growth of the micro-organisms sought to be cultivated.

The impeller means may be located at either open end portion of the baffle; if the latter has an upright orientation, the impeller means may be located at the upper or the lower end portion of the baffle.

To obtain a self-aspiration of the gaseous phase, i.e. aspiration of the gaseous phase into the vessel without expenditure of power, and at the same time to obtain particularly good aeration of the liquid phase by the aspirated gaseous phase, aspirating means may be provided which is of the type to be discussed in detail later, and which may also be located at either of the open end portions of the baffle.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

FIG. 1 is a vertical section through an apparatus according to one embodiment of the invention;

FIG. 2 is a view similar to FIG. 1, but more diagrammatic, showing another embodiment of the invention;

FIG. 3 is a section taken on line III—III of FIG. 1;

FIG. 4 is a view similar to FIG. 3, but showing another embodiment of the invention;

DESCRIPTION OF THE PREFERRED EMBODIMENTS

Figure 5:
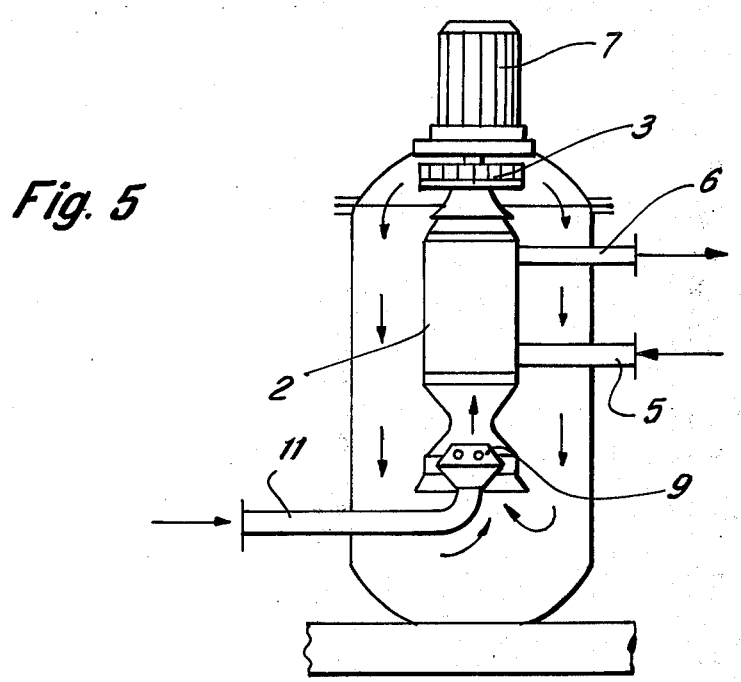
FIG. 5 is a view analogous to FIG. 2, showing still an additional embodiment of the invention.

Referring to the drawing in detail, and describing firstly the embodiment in FIGS. 1 and 3, it is pointed out that reference numeral 1 identifies the generally cylindrical housing of an upright fermenter vessel which carries in its upper cover a foam separator 8 of known construction. During the fermentation operation, foam tends to develop in such vessels, and it is the purpose of the device 8 to break up the foam.

Mounted in the interior of the housing 1 is an upright tubular guide baffle 2 having an outer tubular member 2a within which there is arranged a bundle of tubes 4. These tubes 4 are secured in header members 2b which are mounted in the upper and lower end portions of the tubular member 2a and which thus close off the interior of the latter to form a sealed chamber 2c through which the tubes 4 extend. The opposite ends of the tubes 4 penetrate the header members 2a and are open so as to communicate with the interior space 1a of the housing 1. An inlet conduit 5 and an outlet conduit 6, both in communication with a not illustrated source of cooling fluid (e.g. water) also communicate with the sealed chamber 2c so as to circulate cooling fluid through the same in heat-exchanging contact with the tubes 4.

Arranged at the lower end of the guide baffle 2 is an impeller 3 which is driven by a motor 7 in a manner not illustrated but fully known per se. As the arrows indicate, the impeller 3 draws the liquid contained in the space 1a downwardly through the tubes 4, so that it becomes cooled by indirect heat exchange with the cooling fluid in the chamber 2c, and then expels it laterally so that it rises again in the space 1a.

Reference numeral 11 identifies an inlet conduit which communicates with a source of aeration gas, i.e. with the ambient atmosphere. Located within the downwardly converging lower end of the tubular member 2a, above the impeller 3, is a device 9 which serves —when the impeller 3 operates— to aspirate the aeration gas through the conduit 11 into the stream of liquid which flows downwardly out of the tubes 4, so that the gas and liquid are intimately mixed as they pass through the impeller and before they are laterally ejected from the same. Details of the device 9 will be described with reference to some of the following Figures; however, the device 9 could be omitted and a source of gas under pressure could be connected with the conduit 11 so that the same would discharge the gas into the liquid stream ahead of the impeller 3.

The sectional view of FIG. 3 shows that the tubes 4 may be of circular cross-section, whereas the sectional view of FIG. 4 shows that they may have other cross-sectional configurations, specifically an elongated oval as indicated for the tubes 4a in FIG. 4.

While water may be used to circulate around the tubes 4 or 4a for cooling purposes, any other cooling medium could be employed. The chamber 2c could also be used for direct evaporation of a cooling medium, such as for example ammonia or freon, in which case very large amounts of heat can be readily removed from the liquid contents of the housing 1.

The embodiment of FIG. 2 is largely similar to that of FIG. 1, except that the device 9 is here installed at the end of the tubular member 2a which is remote from the impeller 3, i.e. at the upper end. The device 9 is of the type that will be described with reference to FIG. 7, as is the one in FIG. 1, but either of them could be replaced with the analogous device that is illustrated and described with reference to FIG. 6. The other elements in FIG. 2 are the same as in FIG. 1.

FIG. 5 shows an embodiment that is similar to the one illustrated in FIG. 2, so that like reference numerals have been used to designate like elements. However, FIG. 5 illustrates that the motor 7 can also be located at the upper end of the baffle 2 (or at least in the general vicinity of this upper end), whereas the device 9 —again the same as described with reference to FIG. 7— can also be located at the lower end of the baffle. The flow direction of the vessel contents is here reversed, as compared to FIG. 2.

In FIGS. 2, 5, 6 and 7 the arrangement of the tubes 4 or 4a in the tubular member of the baffle 2 is the same as shown in FIG. 1. For this reason, the tubes have not been illustrated in FIGS. 2, 5, 6 and 7.

Figure 6:
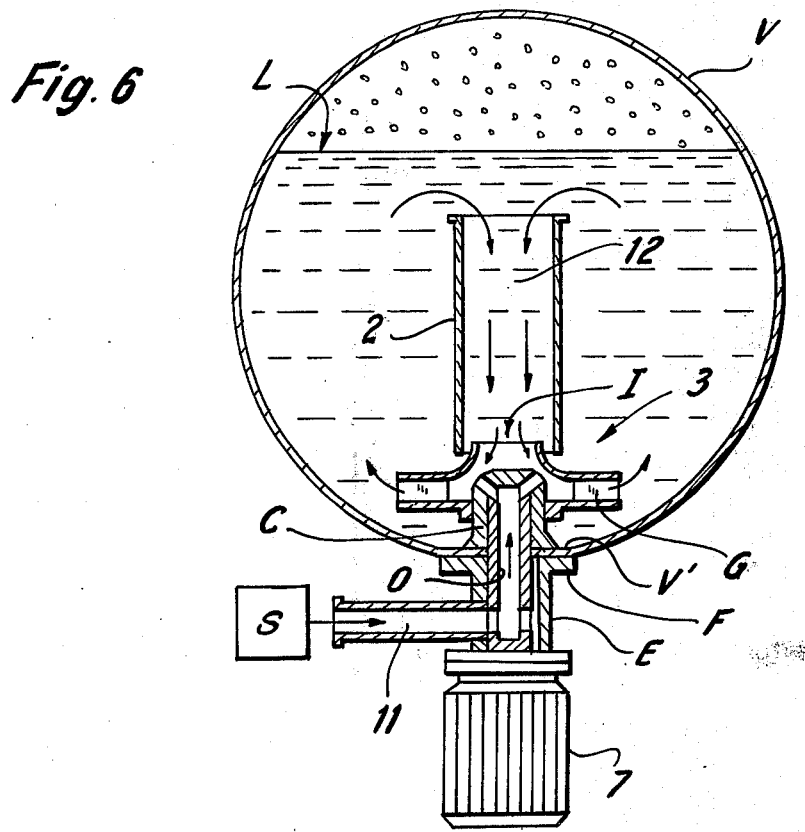
FIG. 6 is a vertical section through an apparatus according to yet another embodiment of the invention.

FIG. 6 shows an embodiment wherein it is shown that the vessel V can also be of spherical configuration and wherein the somewhat diagrammatically illustrated impeller 3 is mounted to a flange V' of the vessel V. An inlet conduit 11 is provided which communicates with a source S of gas, such as the ambient atmosphere. The output shaft O is driven in rotation by the diagrammatically illustrated motor 7. A support element E journals the shaft O for rotation and is provided with a flange F by means of which the arrangement can be secured to the vessel flange V', for instance by bolting it thereto.

The baffle 2 extends from the inlet opening I of the impeller 3 upwardly to provide a path for the liquid which is being drawn into the impeller. The baffle 2 makes it possible to draw liquid from or from near the level L of the body of liquid to assure that those components of the vessel contents which tend to float up are also being drawn into the impeller 3.

The impeller 3 is hollow and its interior communicates with the inlet I and also with outlet openings located at the periphery of the impeller 3. The interior of the impeller is subdivided by substantially radially extending guide vanes G. The shaft O is hollow and its interior communicates with the conduit 11. Its upper end is surrounded by a cap C having outlet openings which open into the Venturi-shaped throat of the inlet I.

When the impeller 3 rotates, centrifugal action expels liquid from the interior of the impeller through the peripheral openings. This causes a suction in the throat of the Venturi-shaped inlet I, and thus draws liquid down into the latter through the tubes (not shown) in the baffle 2. At the same time, the suction prevailing in the throat also acts via the apertures in cap C upon the shaft O and the conduit 11, and aspirates gas (e.g. air) into the throat where it becomes mixed with the stream of liquid, to be expelled with the same from the impeller 3 at the outlet openings located on the periphery of the impeller.

Figure 7:
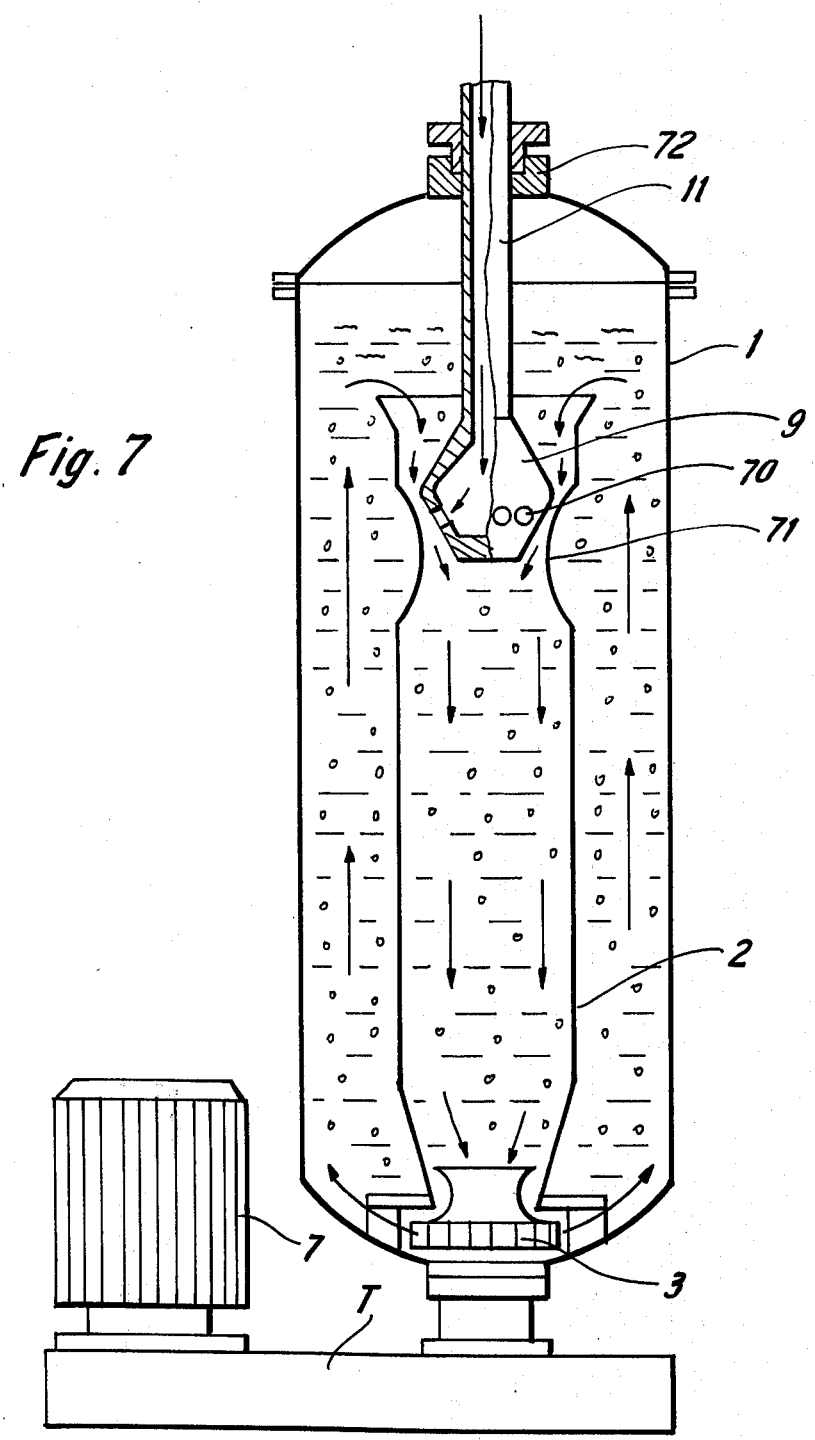
FIG. 7 is another vertical section through an apparatus which incorporates still an additional embodiment of the invention.

In FIG. 7 finally I have shown the vessel 1 to be again of cylindrical shape and to have an upright orientation. In the region of the bottom of the vessel there is located in the interior the impeller 3 which axially draws the vessel contents, i.e. the liquid and gaseous phase, and which expels the contents in radial direction, as already described. The electromotor 7 drives the impeller 3 via a transmission T.

Located within the vessel 1, extending axially thereof in upright direction and having its lower open end located above the impeller 3 is again the tubular guide baffle 2 which extends into the upper region of the vessel 1 and which has a constriction 71 at its upper end. Located in this upper end is the gas-admitting device 9 which is constructed as a hollow double-conical member and which is mounted on the hollow supply conduit 11, which is in turn so mounted that it can be shifted vertically, that is axially of the baffle 2. The device 9 defines with the throat of the constriction 71 an annular gap the cross-section of which can be varied when the device 9 and the conduit 11 are shifted in axial direction. The device 9 has gas outlet openings 70 which are located in a common plane transverse to the elongation of the device 9. The conduit 11 is mounted in a stuffing box 72 which serves to seal the upper end of the vessel 1 and also to hold the conduit 11 for such shiftable displacement.

The liquid phase which is to have a gaseous phase admixed with it, i.e. the nutrient medium for growth of micro-organisms, is admitted into the vessel 1 either batch-wise or continuously, and a gaseous phase —such as air— is in communication with the conduit 11. When the impeller 3 is operated, the liquid phase is drawn axially in downward direction through the baffle 2, entering the latter at the upper open end, and is expelled radially at the bottom end thereof. It therefore can move upwardly outside the guide baffle 2, whereas inside the guide baffle 2 it travels downwardly through the tubes (not shown) therein. Depending upon the axial position of the device 9, the latter defines with the wall bounding the constriction 71 of the guide baffle 2 an annular gap of greater or lesser cross-section, in which the liquid phase reaches its highest flow speed, so that a suction develops at the location at which the openings 70 are provided. Since the device 9 is located in the upper region of the vessel 1, the hydrostatic pressure which heretofore was objectionable in the prior art cannot act to prevent the ready introduction of the gaseous phase, especially as there is in this region an underpressure resulting from the Venturi effect of the flow of the liquid phase through the throat of the constriction.

The suction effect exerted by the gaseous phase which rushes through the annular gap where the constriction 71 forms the throat, is sufficient to draw air or other gaseous medium through the openings 70, the device 9 and the conduit 11. This substantially increases the economy of operation of the device, since no energy is required for a blower or the like to blow the gaseous phase into the vessel 1, and it also reduces the expenses of constructing the device since no blower or similar element need be provided.

It will be understood that each of the elements described above, or two or more together, may also find a useful application in other types of constructions differing from the types described above.

While the invention has been illustrated and described as embodied in a fermenter, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An apparatus for cultivation of micro-organisms, comprising a vessel having a chamber for a cultivating liquid; a tubular guide baffle element mounted in said chamber and having spaced open end portions; means for maintaining the liquid at a constant uniform temperature required for optimum cultivation of the micro-organisms, including heat-exchange tubes mounted in the guide baffle element and subdividing the interior thereof into at least one first compartment for the liquid and at least one sealed second compartment for a heat-exchange medium, and means for circulating the heat-exchange medium through said second compartment; means for advancing the liquid through said first compartment and axially of said tubular guide baffle element, including an impeller element located at one of said open end portions of said guide baffle element; and aspirating means for introducing into the liquid a gaseous medium which enhances the cultivation of the micro-organisms, including a source of the gaseous medium, one of said elements forming a Venturi passage comprised of a smoothly converging upstream passage portion, a smoothly diverging downstream passage portion and an intermediate constricted middle passage portion forming a throat, said Venturi passage constituting means for effecting the flow of said gaseous medium from the exterior of said vessel through said aspirating means into said passage by developing a Venturi suction force within the cultivating liquid flowing through said throat.

2. An apparatus as defined in claim 1, wherein said vessel is of cylindrical shape.

3. An apparatus as defined in claim 1, wherein said vessel is of spherical shape.

4. An apparatus as defined in claim 1, wherein said heat-exchange tubes are of circular cross-section.

5. An apparatus as defined in claim 1, wherein said heat-exchange tubes are of substantially oval cross-section.

6. An apparatus as defined in claim 1 wherein said vessel and baffle element have an upright orientation, and wherein said one open end portion is a lower end portion of said baffle element.

7. An apparatus as defined in claim 1, wherein said vessel and baffle element have an upright orientation, and wherein said one open end portion is an upper end portion of said baffle element.

8. An apparatus as defined in claim 1, wherein said guide baffle includes header members extending across the interior of said baffle element inwardly of said open end portion and defining said second sealed compartment; and wherein said heat-exchange tubes extend through said second compartment and have open ends which penetrate the respective header members.

9. An apparatus as defined in claim 1, wherein said vessel and baffle element have an upright orientation; and wherein said one open end portion is a lower end portion of said baffle element, and said aspirating means is located at the upper open end portion of said baffle element.

10. An apparatus as defined in claim 1, wherein said vessel and baffle element have an upright orientation; and wherein said one open end portion is an upper open end portion of said baffle element, and said aspirating means is located at the lower open end portion of said baffle element.

11. An apparatus as defined in claim 1, wherein said aspirating means comprises a body located in said Venturi passage.

12. An apparatus as defined in claim 1, wherein said impeller element is a hollow substantially disk-shaped rotor mounted for rotation in said interior and having a hub, a periphery formed with outlet openings communicating with the interior of said rotor and of said vessel; wherein said Venturi passage is formed at an axial end of said rotor and communicates with said baffle element so as to draw the liquid from the same and eject it via said openings into the interior of said vessel; and wherein said aspirating means comprises a gas passage extending through said hub and communicating with said Venturi passage, whereby suction which is centrifugally created in said throat during rotation of said rotor aspirates said liquid through said throat and gas through said passage so that the aspirated gas becomes admixed with the aspirated liquid for joint centrifugal ejection through said outlet openings.

* * * * *